United States Patent
Tao et al.

(10) Patent No.: US 12,376,587 B2
(45) Date of Patent: Aug. 5, 2025

(54) BIO-BASED MATERIAL WITH ANTIBACTERIAL EFFECT AND USE THEREOF

(71) Applicant: THE HONG KONG RESEARCH INSTITUTE OF TEXTILES AND APPAREL LIMITED, Hong Kong (CN)

(72) Inventors: Xiaoming Tao, Hong Kong (CN); Xingxing Yang, Hong Kong (CN); Ziheng Zhang, Hong Kong (CN); Jun Li, Hong Kong (CN); Shirui Liu, Hong Kong (CN); Linlin Ma, Hong Kong (CN); Bin Fei, Hong Kong (CN); Hang Mei Leung, Hong Kong (CN)

(73) Assignee: The Hong Kong Research Institute of Textiles and Apparel Limited, Hong Kong (CN)

(*) Notice: Subject to any disclaimer, the term of this patent is extended or adjusted under 35 U.S.C. 154(b) by 743 days.

(21) Appl. No.: 17/053,702

(22) PCT Filed: Jun. 15, 2018

(86) PCT No.: PCT/CN2018/085991
§ 371 (c)(1),
(2) Date: Nov. 6, 2020

(87) PCT Pub. No.: WO2019/213833
PCT Pub. Date: Nov. 14, 2019

(65) Prior Publication Data
US 2021/0084897 A1 Mar. 25, 2021

(30) Foreign Application Priority Data

May 8, 2018 (CO) .......................... 201810431508

(51) Int. Cl.
| | | |
|---|---|---|
| *A01N 37/36* | (2006.01) | |
| *A61L 24/00* | (2006.01) | |
| *A61L 24/04* | (2006.01) | |
| *A61L 26/00* | (2006.01) | |
| *A61L 27/18* | (2006.01) | |
| *A61L 27/54* | (2006.01) | |
| *A61L 31/10* | (2006.01) | |
| *A61L 31/16* | (2006.01) | |
| *C07C 69/675* | (2006.01) | |
| *C08G 63/06* | (2006.01) | |

(52) U.S. Cl.
CPC .......... *A01N 37/36* (2013.01); *A61L 24/0015* (2013.01); *A61L 24/046* (2013.01); *A61L 26/0019* (2013.01); *A61L 26/0066* (2013.01); *A61L 27/18* (2013.01); *A61L 27/54* (2013.01); *A61L 31/10* (2013.01); *A61L 31/16* (2013.01); *C07C 69/675* (2013.01); *C08G 63/06* (2013.01); *A61L 2300/404* (2013.01)

(58) Field of Classification Search
CPC .. C08L 67/04; A61L 27/18; A61L 2/23; A61L 27/26; A61L 24/00; A61L 24/04; A61L 26/00; A61L 27/54; A61L 31/10; A61L 31/16; A01N 37/36; C08G 63/06; C07C 69/675
See application file for complete search history.

(56) References Cited

U.S. PATENT DOCUMENTS

| | | | |
|---|---|---|---|
| 7,807,722 B2 | 10/2010 | Pacetti | |
| 2017/0196826 A1* | 7/2017 | Pirttilä | ................... A01N 37/36 |

FOREIGN PATENT DOCUMENTS

| | | |
|---|---|---|
| CN | 1896142 A | 1/2007 |
| CN | 104071861 A | 10/2014 |
| CN | 105907063 A | 8/2016 |
| CN | 106479097 A | 3/2017 |
| CN | 107286611 A | 10/2017 |
| CN | 107385628 A | 11/2017 |
| CN | 107587250 A | 1/2018 |
| JP | H05260984 * | 10/1993 ................ C12P 7/42 |
| WO | WO 2016/012657 A1 | 1/2016 |

OTHER PUBLICATIONS

JPH05260984 (translation), 1993. (Year: 1993).*
JPH10265378A (translation), 1998. (Year: 1998).*
Chan, Int. J. of Polymer Sci., 2011, 1, p. 1-9. (Year: 2011).*
Para, J. Polym. Environ, 2011, 19, p. 918-925. (Year: 2011).*
Chinese Office Action dated Aug. 30, 2021 in connection with Chinese Application No. 201810431508.5.

(Continued)

*Primary Examiner* — Michael G. Hartley
*Assistant Examiner* — Leah H Schlientz
(74) *Attorney, Agent, or Firm* — Wolf, Greenfield & Sacks, P.C.

(57) ABSTRACT

Provided is a bio-based material having an antibacterial effect, comprising a polymer represented by a formula (1) or a mixture of the polymer represented by the formula (1) and polyethylene glycol as an antibacterial active ingredient. The use of the bio-based material is also mentioned. The antibacterial bio-based material has excellent, stable and long-lasting antibacterial activity, and has remarkable antibacterial effects against various bacteria and fungi. The antibacterial bio-based material also has excellent biodegradability and biocompatibility, is derived from bio-based products produced by microbial fermentation, has high safety and is suitable for industrial production and large-scale use.

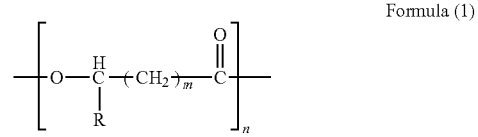

Formula (1)

14 Claims, 1 Drawing Sheet

(56) References Cited

OTHER PUBLICATIONS

Written Opinion mailed Jan. 21, 2019 in connection with International Application No. PCT/CN2018/085991.
International Preliminary Report on Patentability mailed Nov. 19, 2020 in connection with International Application No. PCT/CN2018/085991.
Abdelwahab et al., Poly (3-hydroxybutyrate)/polyethylene glycol-NiO nanocomposite for NOR delivery: Antibacterial activity and cytotoxic effect against cancer cell lines. International journal of biological macromolecules. Jul. 15, 2018;114:717-27. doi: 10.1016/j.ijbiomac.2018.03.050. Epub Mar. 13, 2018.
English translation of International Search Report and Written Opinion (EN translation of ISR only) for Application No. PCT/CN2018/085991, dated Jan. 21, 2019.
CN 201810431508.5, Aug. 30, 2021, Chinese Office Action.
PCT/CN2018/085991, Jan. 21,2019, Written Opinion.
PCT/CN2018/085991, Nov. 19, 2020, International Preliminary Report on Patentability.
Zhang et al., Mechanistic Study of Synergistic Antimicrobial Effects between Poly (3-hydroxybutyrate) Oligomer and Polyethylene Glycol. Polymers. MDPI. Nov. 2, 2020;12(2735). 12 Pages.
Chinese Office Action dated Apr. 28, 2018, in connection with Chinese Application No. 201610327672.2, with English translation thereof.

\* cited by examiner

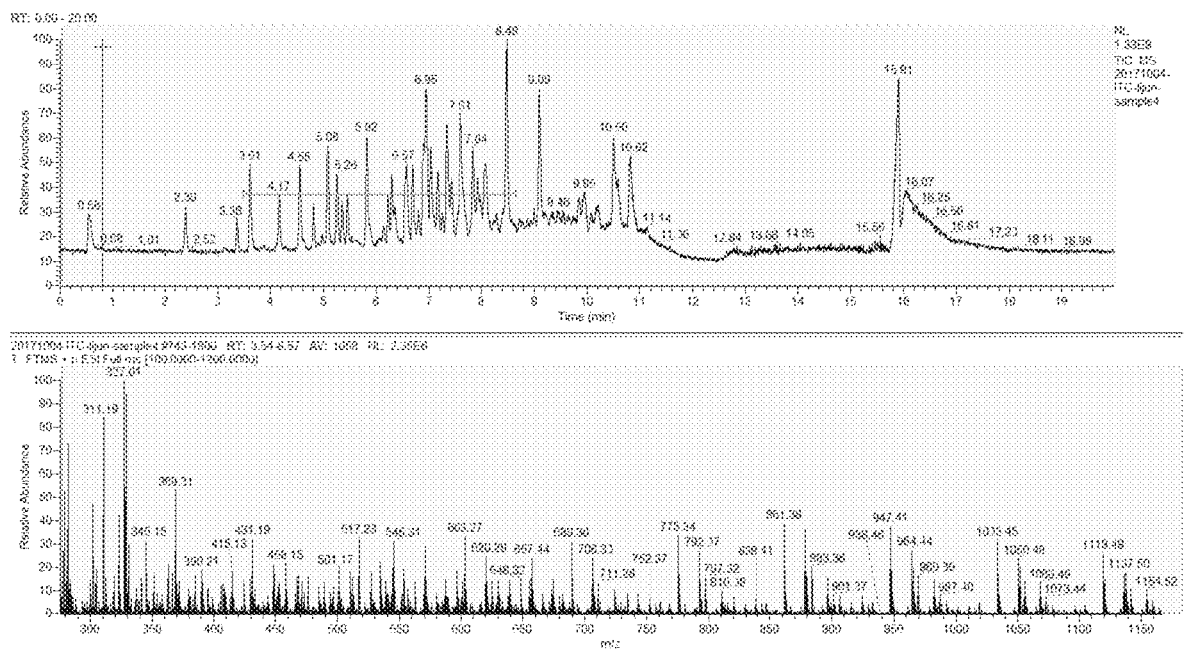

BIO-BASED MATERIAL WITH ANTIBACTERIAL EFFECT AND USE THEREOF

CROSS-REFERENCE TO RELATED APPLICATION(S)

This application is based upon and claims priority to PCT patent application No. PCT/CN2018/085991, filed on Jun. 15, 2018, which claims priority to Chinese Application No. 201810431508.5 filed May 8, 2018, the entire contents of which are incorporated herein by reference for all purposes.

TECHNICAL FIELD

The present disclosure relates to the field of antibacterial materials, in particular to a bio-based polymer material with antibacterial effect and its use in preparing antibacterial materials.

BACKGROUND

There are a large number of microorganisms such as bacteria, fungi, and viruses in the environment where people live. When they multiply under certain conditions, they will not only cause discoloration, mold, and degradation of materials, but also threaten human health. With the improvement of living standards, people have higher and higher requirements for the quality of the living environment and sanitary conditions. Therefore, the research and development of antibacterial agents and antibacterial materials has extremely important significance.

Antibacterial agents are mainly classed into three types: inorganic antibacterial agents, organic antibacterial agents and natural antibacterial agents. The antibacterial active ingredients used in inorganic antibacterial agents mainly include metal ions such as silver and zinc and metal salt compounds, which have the advantages of good heat resistance, antibacterial durability, and no drug resistance, but their chemical properties are active and unstable and expensive. Organic antibacterial agents refer to an antibacterial agent that uses organic acids, quaternary ammonium salts, benzimidazoles and other organic substances as antibacterial active substances. They have broad antibacterial spectrum, but their antibacterial duration is short, chemical stability is poor, and microorganisms are easy to produce chemical resistance, especially they have poor heat resistance, which limit the application range. Natural antibacterial agents are derived from plants, animals or microorganisms, and effective antibacterial materials are obtained through extraction and purification. The resources are extremely rich, and the natural antibacterial agents are safe, non-toxic and have good antibacterial effects.

Poly 3-hydroxybutyrate (PHB) is a polyester produced by microorganisms. It has excellent biodegradability, biocompatibility and optical activity. It is widely used in the filed such as textiles, food packaging, surgical sutures, and tissue engineering scaffolds. In addition, PHB is resistant to ultraviolet rays and does not easily cause inflammation, Because it is produced by microbial cells, it does not contain toxic substances such as heavy metals, and is an extremely clean polymer material.

SUMMARY

In order to expand the range of antibacterial materials, one of the objectives of the present disclosure is to provide a bio-based material with antibacterial effects.

Another object of the present disclosure is to provide the use of the bio-based material.

The bio-based material with antibacterial effect provided by the present disclosure comprises a polymer represented by formula (1) as an antibacterial active ingredient,

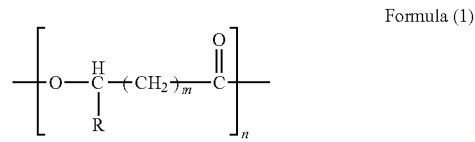

Formula (1)

wherein R represents a $C_1$-$C_5$ alkyl, m represents an integer of 0-3, and n represents an integer of 1-20.

The inventors discovered that the polymer represented by formula (1), such as poly-3-hydroxybutyrate with a low degree of polymerization, has excellent antibacterial activity, thereby providing a novel bio-based antibacterial material.

The bio-based material with antibacterial effect provided by the present disclosure may also comprise polyethylene glycol, and a mixture of polyethylene glycol and the polymer represented by the formula (1) as an antibacterial active ingredient.

The inventors also found that: the polymer represented by formula (1), such as poly-3-hydroxybutyrate with low polymerization degree, is mixed with polyethylene glycol to form a mixture. The two materials act synergistically, and the resulting mixture also has excellent antibacterial activity, which can provide another novel bio-based antibacterial material.

In the bio-based material with antibacterial effect provided by the present disclosure, the polyethylene glycol may be all polyethylene glycol products in a fluid state, and preferably may be polyethylene glycol with a number average molecular weight of 200 to 2000.

In the bio-based material with antibacterial effect provided by the present disclosure, the mass ratio of the polymer represented by formula (1) to polyethylene glycol may be 1:10-10:1.

In the bio-based material with antibacterial effect provided by the present disclosure, the polymer represented by formula (1) and polyethylene glycol in the mixture have a certain viscosity. The mixing time and increase the mixing temperature may be appropriately increased during the mixing stage. Preferably, the preparation process may comprise: mixing the polymer represented by formula (1) and polyethylene glycol at 80-300° C. and stirring for 10 min-6 h.

In the bio-based material with antibacterial effect provided by the present disclosure, the substituent R in formula (1) may preferably be methyl, ethyl, propyl or isopropyl. In the No-based material with antibacterial effect provided by the present disclosure, in in formula (1) can preferably be expressed as 0 or 1.

In the bio-based material with antibacterial effect provided by the present disclosure, the polymer represented by formula (1) may preferably be poly-3-hydroxybutyrate with a low degree of polymerization, which may be synthesized by chemical methods or may be derived from the decomposition of PHB polymer. More preferably, it can be derived from the decomposition of PHB polymer produced by microbial fermentation, and the end groups are hydroxyl and carboxyl, respectively. The poly-3-hydroxybutyrate with a low degree of polymerization may have a degree of polymerization of 1-20, preferably 4-13.

In the bio-based material with antibacterial effect provided by the present 2.0 disclosure, in addition to the polymer represented by formula (1) or a mixture of the polymer represented by formula (1) and polyethylene glycol as an active ingredient, it can comprise any additional ingredients, additives, auxiliary substances, etc. other than the active ingredients used in the existing antibacterial materials, as long as the active ingredients can be made into any form or type of antibacterial material without affecting the antibacterial activity of the active ingredients, which is not limited in the present disclosure.

The present disclosure also provides the use of the bio-based material with antibacterial effect described in any one of the above technical solutions in preparing antibacterial materials.

The present disclosure also provides the use of the polymer represented by formula (1) or the mixture of the polymer represented by formula (1) and polyethylene glycol in the preparation of antibacterial materials,

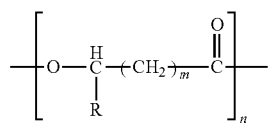

Formula (1)

wherein R represents a $C_1$-$C_5$ alkyl, m represents an integer of 0-3, and n represents an integer of 1-20.

In the use provided by the present disclosure, the polyethylene glycol may be all polyethylene glycol products in a fluid state, and preferably may be polyethylene glycol with a number average molecular weight of 200-2000.

In the use provided by the present disclosure, the mass ratio of the polymer represented by formula (1) to polyethylene glycol may be 1:10-10:1.

In the application provided by the present disclosure, the substituent R in formula (1) may preferably be methyl, ethyl, propyl or isopropyl. In the use provided by the present disclosure, m in formula (1) can be expressed as 0 or 1.

In the use provided by the present disclosure, the polymer represented by formula (1) may preferably be poly-3-hydroxybutyrate with a low degree of polymerization, which may be synthesized by chemical methods or may be derived from the decomposition of PHB polymer. More preferably, it can be derived from the decomposition of PHB polymer produced by microbial fermentation, and the end groups are hydroxyl and carboxyl, respectively. The poly-3-hydroxy/butyrate with a low degree of polymerization may have a degree of polymerization of 1-20, preferably 4-13.

In the above use, the antibacterial material can be of any form or type, as long as the active ingredient can be used in the antibacterial material without affecting the antibacterial activity of the active ingredient.

The antibacterial materials involved in the present disclosure include but are not limited to antibacterial formulations, antibacterial fabrics, sanitary products, medical materials, etc., and are especially suitable for textile, medical and health fields. For example, it can combine with or modify existing polymer textile. For another example, it can be used in antibacterial formulations, and used in preparations such as drugs and disinfectants. For another example, it can be used in medical materials, and can be used as wound covering materials, dressings, surgical sutures, and implant materials, drug carriers and other biomedical materials. The antibacterial material involved in the present disclosure can be used alone or in combination with other antibacterial formulations and antibacterial materials, and can also be used to modify or reform other antibacterial materials.

The bio-based material with antibacterial effect provided by the present disclosure has the following advantages:

(1) It has excellent, stable and long-lasting antibacterial activity, and has significant antibacterial effects against a variety of bacteria and fungi.

(2) In addition to antibacterial activity, the bio-based material of the present disclosure also has excellent properties such as biodegradability, and biocompatibility. It can be derived from bio-based products produced by microbial fermentation, with low cost, high safety, and environmental friendly.

(3) it can be made into various forms or types of antibacterial materials, and can also be used in combination with other antibacterial materials, or used to modify other materials to obtain better antibacterial formulations and antibacterial materials, which greatly enriches the types of antibacterial materials.

(4) The present disclosure does not require a complicated preparation process, and is suitable for industrial production and large-scale use.

DESCRIPTION OF THE DRAWINGS

FIG. 1 is a mass spectrum of the poly-3-hydroxybutyrate of Example 1 having a low polymerization degree.

DETAILED DESCRIPTION

To make the objects, technical solutions, and advantages of the present disclosure clearer, the technical solutions of the exemplary embodiments of the present disclosure will be further described below.

The chemical reagents used in the following examples are commercially available products unless otherwise specified, and the operations or instruments used in the following examples are common operations or instruments in the art unless otherwise specified.

Example 1

The preparation process of poly-3-hydroxybutyrate with a low polymerization degree was as follows: 10 g of PHB masterbatch prepared by microbial method was added into 200 mL chloroform and refluxed for 24 h. Then, the mixture was added into 1 L methanol, filtered, and then the solvent was removed from the filtrate by rotary evaporation, to obtain a poly-3-hydroxybutyrate with a low degree of polymerization. An appropriate amount of poly-3-hydroxybutyrate with a low degree of polymerization was dissolved in 1:1 DCM/methanol, filtered with a 0.45 μm microporous membrane. As shown in FIG. 1, the mass spectrum of poly-3-hydroxybutyrate with a low degree of polymerization was obtained by the mass spectrometer.

It can be seen from the mass spectrum of FIG. 1 that poly-3-hydroxybutyrate with a low degree of polymerization had the repeating unit of the following structure, and the end groups were hydroxyl and carboxyl groups, respectively:

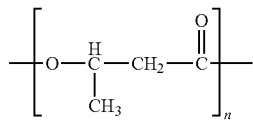

the molecular weight of the repeating unit is 86, and n is 4-13.

Example 2

The poly-3-hydroxybutyrate with a low degree of polymerization of Example 1 was mixed uniformly with PEG with a number average molecular weight of 600 in a mass ratio of 1:1, heated and stirred at 150° C. for 4 hours. Then, it was cooled to room temperature for further use.

Example 3

The poly-3-hydroxybutyrate with a low degree of polymerization of Example 1 was mixed uniformly with PEG with a number average molecular weight of 600 in a mass ratio of 1:10, heated and stirred at 150° C. for 4 hours. Then, it was cooled to room temperature for further use.

Experimental Examples

The poly-3-hydroxybutyrate with a low degree of polymerization of Example 1 and the mixtures of the poly-3-hydroxybutyrate with a low degree of polymerization and PEG of Examples 2 and 3 were diluted to 20 mg/mL, with phosphate buffer. The shaking method (see the Chinese national standard GB15979-2002) was used to detect their antibacterial activity, wherein the PBS group was used as a blank control. The antibacterial performance results obtained were shown in Table 1.

TABLE 1

|  | Antibacterial rate (%) | | |
| --- | --- | --- | --- |
|  | Staphylococcus aureus (Gram-positive bacteria) | Pneumoniae bacteria (Gram-negative bacteria) | Candida albicans (Fungus) |
| Example 1 | >99.99% | 49.6% | 0 |
| Example 2 | >99.99% | 82.60% | 85.6% |
| Example 3 | 92.22% | 99.44% | ND |

From the results in Table 1, it can be seen that poly-3-hydroxybutyrate with low polymerization degree had very excellent antibacterial activity against *Staphylococcus aureus*, and obvious antibacterial activity against *Pneumoniae* bacteria; while the mixture of poly-3-hydroxybutyrate with low polymerization degree and polyethylene glycol had excellent antibacterial activity against both *Staphylococcus aureus* and *Pneumoniae bacillus*. In addition, the mixture had a very significant antibacterial rate against *Candida albicans* and had a broad-spectrum antibacterial effect.

After placing the materials obtained in Examples 1-3 for several months, the antibacterial activity was tested according to the above method. The results were almost the same as the aforementioned test results. It can be seen that their properties were stable, and the antibacterial activity was stable and lasting.

It is not difficult to conclude that the bio-based polymer material of the present disclosure has extremely high application potential in the field of antibacterial formulations and antibacterial materials, especially as medical antibacterial materials.

Although the preferred embodiments of the present disclosure have been disclosed in order to illustrate the present disclosure, those skilled in the art should understand that various modifications, additions and replacements can be made to the present disclosure without departing from the concept and scope of the present disclosure as defined by the claims.

We claim:
1. A bio-based material with antibacterial and antifungal effect comprising a mixture of
   a polymer represented by formula (1) as an antibacterial and antifungal active ingredient,

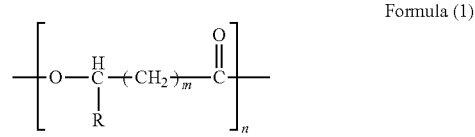

Formula (1)

wherein R represents methyl, m represents 1, n represents an integer of 1-20, and the end groups are hydroxyl and carboxyl groups, respectively; and
polyethylene glycol having a number average molecular weight of 600, and
wherein in the mixture, the mass ratio of the polymer represented by formula (1) to the polyethylene glycol is 1:1.

2. The bio-based material with antibacterial and antifungal effect according to claim 1, wherein the mixture of the polyethylene glycol and the polymer represented by the formula (1) is used as the antibacterial and antifungal active ingredient.

3. The bio-based material with antibacterial and antifungal effect according to claim 1, wherein a preparation process of the mixture comprises mixing the polymer represented by formula (1) and the polyethylene glycol at 80-300° C. and stirring for 10 min-6 h.

4. A method of preparing an antibacterial and antifungal material comprising:
   combining the bio-based material of claim 1 with a substrate.

5. A method of preparing an antibacterial and antifungal material comprising:
   obtaining a polymer represented by formula (1), and
   combining the polymer represented by formula (1) with polyethylene glycol in a mass ratio of the nolvmer represented by formula (1) to the polyethylene glycol of 1:1

Formula (1)

wherein R represents methyl, m represents 1, n represents an integer of 1-20, and the end groups are hydroxyl and carboxyl groups, respectively, and
wherein the polyethylene glycol has a number average molecular weight of 600.

6. The method according to claim 4, wherein the antibacterial and antifungal material is one or more of antibacterial and antifungal formulations, antibacterial and antifungal fabrics, sanitary products and medical materials.

7. The method according to claim 5, wherein the antibacterial and antifungal material is one or more of antibacterial and antifungal formulations, antibacterial and antifungal fabrics, sanitary products and medical materials.

8. The method according to claim 4, wherein the substrate is one or more of a textile, food packaging, wound covering materials, dressings, surgical sutures, implant materials, drug carriers, biomedical materials, and tissue engineering scaffolds.

9. The bio-based material with antibacterial and antifungal effect according to claim 1, wherein in the formula (1), n represents an integer of 4-13.

10. The method according to claim 5, wherein in the formula (1), n represents an integer of 4-13.

11. The bio-based material with antibacterial and antifungal effect according to claim 1, wherein in the formula (1), n represents an integer of 1-6.

12. The method according to claim 5, wherein in the formula (1), n represents an integer of 1-6.

13. The bio-based material with antibacterial and antifungal effect according to claim 1, wherein the bio-based material consists of the mixture.

14. The bio-based material with antibacterial and antifungal effect according to claim 1, wherein the bio-based material consists essentially of the mixture.

* * * * *